United States Patent
Ratulowski et al.

(10) Patent No.: US 9,689,858 B2
(45) Date of Patent: Jun. 27, 2017

(54) METHOD AND APPARATUS FOR MEASURING ASPHALTENE ONSET CONDITIONS AND YIELDS OF CRUDE OILS

(71) Applicant: Schlumberger Technology Corporation, Sugar Land, TX (US)

(72) Inventors: John Ratulowski, Edmonton (CA); Shahnawaz Molla, Edmonton (CA); Vincent Sieben, Edmonton (CA); Farshid Mostowfi, Edmonton (CA); Shawn Taylor, Edmonton (CA); Christopher Harrison, Newton, MA (US); Shunsuke Fukagawa, Arlington, MA (US); Elizabeth Smythe, Cambridge, MA (US); Matthew Sullivan, Westwood, MA (US); John Meier, Boston, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/919,504

(22) Filed: Oct. 21, 2015

(65) Prior Publication Data

US 2017/0115266 A1 Apr. 27, 2017

(51) Int. Cl.
*G01N 33/28* (2006.01)
*G01V 8/02* (2006.01)

(52) U.S. Cl.
CPC ..... *G01N 33/2823* (2013.01); *G01N 33/2835* (2013.01); *G01V 8/02* (2013.01)

(58) Field of Classification Search
CPC .... G01N 33/2823; G01N 21/85; G01N 21/27; G01N 21/3577; G01N 21/552;

(Continued)

(56) References Cited

U.S. PATENT DOCUMENTS 8,269,961 B2 * 9/2012 Mostowfi ........... G01N 33/2823
356/246
9,068,962 B2 6/2015 Schneider et al.
(Continued)

FOREIGN PATENT DOCUMENTS

WO 2001020322 A1 3/2001

OTHER PUBLICATIONS

Adyani, W. N., W. A. W. Daud, et al. (2011). A Systematic Approach to Evaluate Asphaltene Precipitation during CO2 Injection. SPE Enhanced Oil Recovery Conference. Kuala Lumpur, Malaysia, Society of Petroleum Engineers. (27 pages).

(Continued)

*Primary Examiner* — Michael P Stafira
(74) *Attorney, Agent, or Firm* — Trevor G. Grove (57) ABSTRACT

A method for determining an asphaltene onset condition of a crude oil is provided. The method includes receiving a crude oil within a downhole tool inside a well and taking a first measurement of an optical property of the received crude oil. The method also includes lowering the pressure or temperature of the crude oil after taking the first measurement of the optical property to cause aggregation of asphaltenes in the crude oil, and then separating aggregated asphaltenes from the crude oil. Further, the method includes taking a second measurement of the optical property of the crude oil within the downhole tool after separating aggregated asphaltenes from the crude oil and determining an asphaltene onset condition of the crude oil through comparison of the first and second measurements of the optical property. Additional methods, systems, and devices are also disclosed.

11 Claims, 9 Drawing Sheets

(58) Field of Classification Search
CPC ...... G01N 21/359; G01N 21/31; G01N 21/15; G01N 21/64; G01N 1/00; G01N 33/28; G01N 2201/12; G01N 33/24; G01N 15/082; G01N 21/25
See application file for complete search history.

(56) References Cited

U.S. PATENT DOCUMENTS

| | | | |
|---|---|---|---|
| 2009/0091320 A1* | 4/2009 | Flaum | G01V 3/32 324/303 |
| 2011/0093200 A1* | 4/2011 | Hsu | E21B 47/10 702/8 |
| 2013/0188169 A1* | 7/2013 | Harrison | G01N 21/85 356/36 |
| 2014/0369889 A1* | 12/2014 | Mostowfi | G01N 33/2823 422/82.09 |
| 2016/0097757 A1* | 4/2016 | Sieben | G01N 1/28 436/60 |

OTHER PUBLICATIONS

Gonzalez, D. L., E. Mahmoodaghdam, et al. (2012). Effects of Gas Additions to Deepwater Gulf of Mexico Reservoir Oil: Experimental Investigation of Asphaltene Precipitation and Deposition. SPE Annual Technical Conference and Exhibition. San Antonio, Texas, USA, Society of Petroleum Engineers. (11 pages).
Hammami, A., C. H. Phelps, et al. (1999). "Asphaltene Precipitation from Live Oils: An Experimental Investigation of Onset Conditions and Reversibility." Energy & Fuels 14(1): 14-18.
Jamaluddin, A. K. M., J. Creek, et al. (2001). A Comparison of Various Laboratory Techniques to Measure Thermodynamic Asphaltene Instability. SPE Asia Pacific Improved Oil Recovery Conference. Kuala Lumpur, Malaysia Society of Petroleum Engineers. (17 pages).
Jamaluddin, A. K. M., N. Joshi, et al. (2002). An Investigation of Asphaltene Instability Under Nitrogen Injection. SPE International Petroleum Conference and Exhibition in Mexico. Villahermosa, Mexico, Copyright 2002, Society of Petroleum Engineers Inc. (10 pages).
Joshi, N. B., O. C. Mullins, et al. (2001). "Asphaltene Precipitation from Live Crude Oil." Energy & Fuels 15(4): 979-986.
Kalantari-Dahaghi, A., V. Gholami, et al. (2008). "Formation Damage Through Asphaltene Precipitation Resulting From CO2 Gas Injection in Iranian Carbonate Reservoirs." SPE Production & Operations 23(2): 210-214.
Jill S. Buckley (1999). "Predicting the Onset of Asphaltene Precipitation from Refractive Index Measurements." Energy & Fuels 13: 328-332.

* cited by examiner

METHOD AND APPARATUS FOR MEASURING ASPHALTENE ONSET CONDITIONS AND YIELDS OF CRUDE OILS

BACKGROUND

Wells are generally drilled into subsurface rocks to access fluids, such as hydrocarbons, stored in subterranean formations. The formations penetrated by a well can be evaluated for various purposes, including for identifying hydrocarbon reservoirs within the formations. During drilling operations, one or more drilling tools in a drill string may be used to test or sample the formations. Following removal of the drill string, a wireline tool may also be run into the well to test or sample the formations. These drilling tools and wireline tools, as well as other wellbore tools conveyed on coiled tubing, drill pipe, casing or other means of conveyance, are also referred to herein as "downhole tools." Certain downhole tools may include two or more integrated collar assemblies, each for performing a separate function, and a downhole tool may be employed alone or in combination with other downhole tools in a downhole tool string.

Formation evaluation may involve drawing fluid from the formation into a downhole tool. In some instances, the fluid drawn from the formation is retained within the downhole tool for later testing outside of the well. In other instances, downhole fluid analysis may be used to test the fluid while it remains in the well. Such analysis can be used to provide information on certain fluid properties in real time without the delay associated with returning fluid samples to the surface.

Asphaltenes are generally the heaviest fraction and the most polar component in a petroleum mixture. Asphaltenes are insoluble in n-alkanes and soluble in toluene. They can be aggregated as solid particles under certain pressure and temperature conditions in some crude oils, or by injecting a solvent. During production, the solubility of asphaltenes in crude oil decreases with pressure as the fluid travels through the reservoir and the wellbore. Asphaltene deposition can sometimes negatively impact production, such as by plugging pipelines and impairing the flow of hydrocarbons through formations and into wells.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one embodiment of the present disclosure, a method includes receiving a crude oil in a downhole tool inside a well and taking a first measurement of an optical property of the crude oil. The method also includes aggregating asphaltenes in the crude oil after taking the first measurement of the optical property and then separating aggregated asphaltenes from the crude oil. A second measurement of the optical property of the crude oil is taken after separating the aggregated asphaltenes and an asphaltene onset condition of the crude oil is determined through comparison of the first and second measurements of the optical property.

In another embodiment, a method includes receiving crude oil within a measurement apparatus and determining an asphaltene onset pressure of the crude oil. Determining the asphaltene onset pressure includes changing pressure of the received crude oil within the measurement apparatus and passing the crude oil through a filter of the measurement apparatus. Determining the asphaltene onset pressure also includes tracking, over different pressures, the optical density of the crude oil after the crude oil has passed through the filter and identifying the asphaltene onset pressure from the tracked optical density over the different pressures.

In a further embodiment, an apparatus includes a downhole sampling tool and a controller. The downhole sampling tool includes an intake for receiving a formation fluid and a downhole fluid analysis module having a spectrometer for measuring an optical property of the received formation fluid. The controller can be operated to cause aggregation of asphaltenes in the received formation fluid within the downhole sampling tool by lowering a pressure of the received formation fluid, to measure the optical property of the received formation fluid, and to determine asphaltene content of the received formation fluid using the measured optical property.

Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

The present disclosure generally relates to determining asphaltene characteristics of a fluid. More particularly, certain embodiments of the present disclosure relate to determining asphaltene onset conditions and asphaltene content of crude oils. Further, in at least some instances, these characteristics can be determined for crude oils at high-pressure and high-temperature conditions, such as live crude oils downhole within wells. For example, the present techniques can be used to detect asphaltene onset pressure (AOP) in live crude oils and to measure weight concentration of aggregated asphaltenes (which may also be referred to as a yield measurement) at different pressures above bubble point pressure. As described in detail below, in certain embodiments crude oils are received in measurement apparatuses (which may be provided in a downhole tool, such as those described below, or at the surface) and conditions in the apparatuses are then changed to cause aggregation of asphaltenes within the crude oils. The aggregated asphaltenes are removed from the crude oils and optical characteristics, such as optical densities, of the crude oils can be used to determine asphaltene onset conditions or yields. More specifically, in at least one embodiment, an optical spectroscopy technique for measuring asphaltene onset condition and yield in crude oil includes comparing optical densities of the crude oil measured before and after removal of aggregated asphaltenes from the crude oil.

Figure 1:
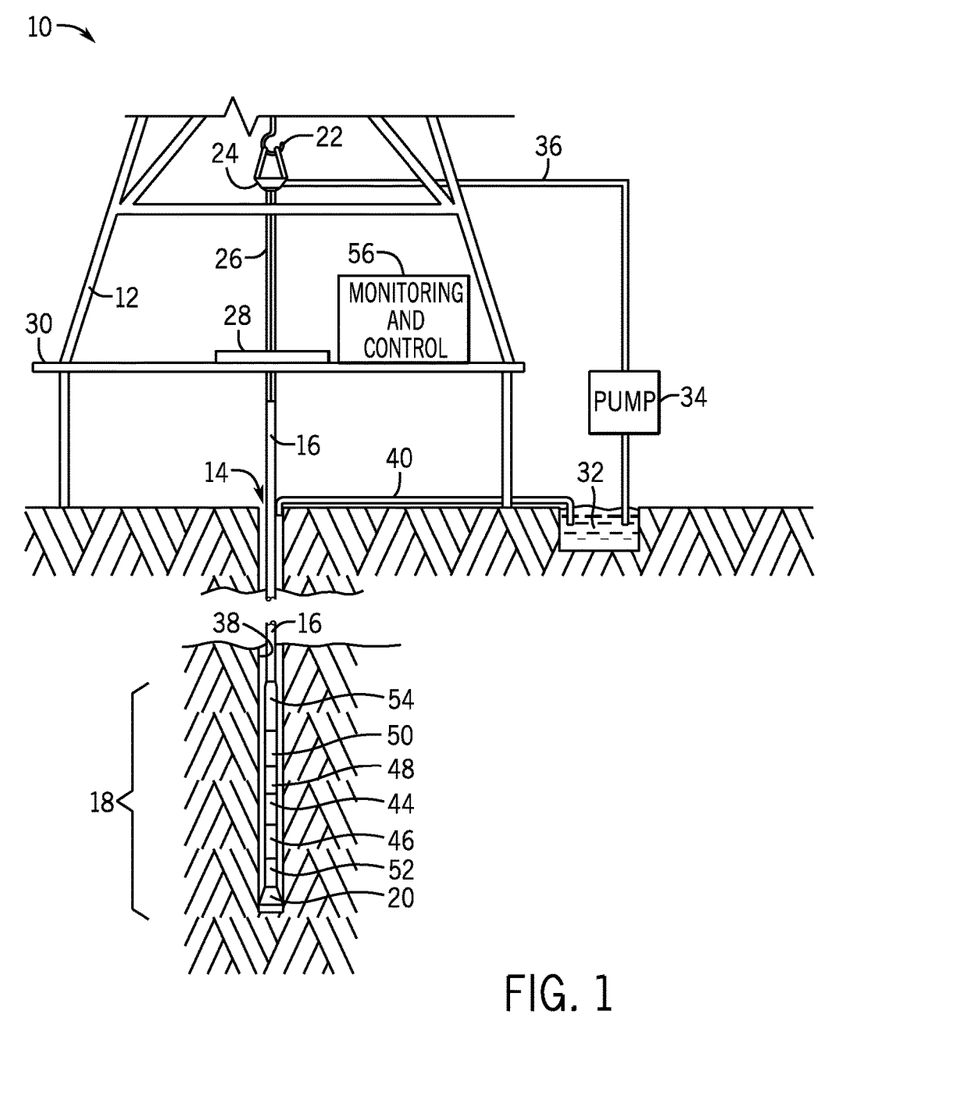
FIG. 1 generally depicts a drilling system having a fluid sampling tool in a drill string in accordance with one embodiment of the present disclosure.

Turning now to the drawings, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 includes a drilling rig 12 positioned over a well 14. Although depicted as an onshore drilling system 10, it is noted that the drilling system could instead be an offshore drilling system. The drilling rig 12 supports a drill string 16 that includes a bottomhole assembly 18 having a drill bit 20. The drilling rig 12 can rotate the drill string 16 (and its drill bit 20) to drill the well 14.

The drill string 16 is suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 is coupled to the drill string 16, and the swivel 24 allows the kelly 26 and the drill string 16 to rotate with respect to the hook 22. In the presently illustrated embodiment, a rotary table 28 on a drill floor 30 of the drilling rig 12 is constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 is circulated through the well 14 by a pump 34. The drilling fluid 32 is pumped from a mud pit (or some other reservoir, such as a mud tank) into the drill string 16 through a supply conduit 36, the swivel 24, and the kelly 26. The drilling fluid 32 exits near the bottom of the drill string 16 (e.g., at the drill bit 20) and returns to the surface through the annulus 38 between the wellbore and the drill string 16. A return conduit 40 transmits the returning drilling fluid 32 away from the well 14. In some embodiments, the returning drilling fluid 32 is cleansed (e.g., via one or more shale shakers, desanders, or desilters) and reused in the well 14.

In addition to the drill bit 20, the bottomhole assembly 18 also includes various instruments that measure information of interest within the well 14. For example, as depicted in FIG. 1, the bottomhole assembly 18 includes a logging-while-drilling (LWD) module 44 and a measurement-while-drilling (MWD) module 46. Both modules include sensors, housed in drill collars, that collect data and enable the creation of measurement logs in real-time during a drilling operation. The modules could also include memory devices for storing the measured data. The LWD module 44 includes sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 includes sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in greater detail below, one or more of the modules 44, 46, and 48 is or includes a fluid sampling tool configured to obtain a sample of a fluid from a subterranean formation and perform downhole fluid analysis to measure an optical property (e.g., optical density) of the sampled fluid, which can then be used to determine asphaltene onset conditions and asphaltene content of the fluid.

The bottomhole assembly 18 can also include other modules. As depicted in FIG. 1 by way of example, such other modules include a power module 50, a steering module 52, and a communication module 54. In one embodiment, the power module 50 includes a generator (such as a turbine) driven by flow of drilling mud through the drill string 16. In other embodiments the power module 50 could also or instead include other forms of power storage or generation, such as batteries or fuel cells. The steering module 52 may include a rotary-steerable system that facilitates directional drilling of the well 14. The communication module 54 enables communication of data (e.g., data collected by the LWD module 44 and the MWD module 46) between the bottomhole assembly 18 and the surface. In one embodiment, the communication module 54 communicates via mud pulse telemetry, in which the communication module 54 uses the drilling fluid 32 in the drill string as a propagation medium for a pressure wave encoding the data to be transmitted.

The drilling system 10 also includes a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
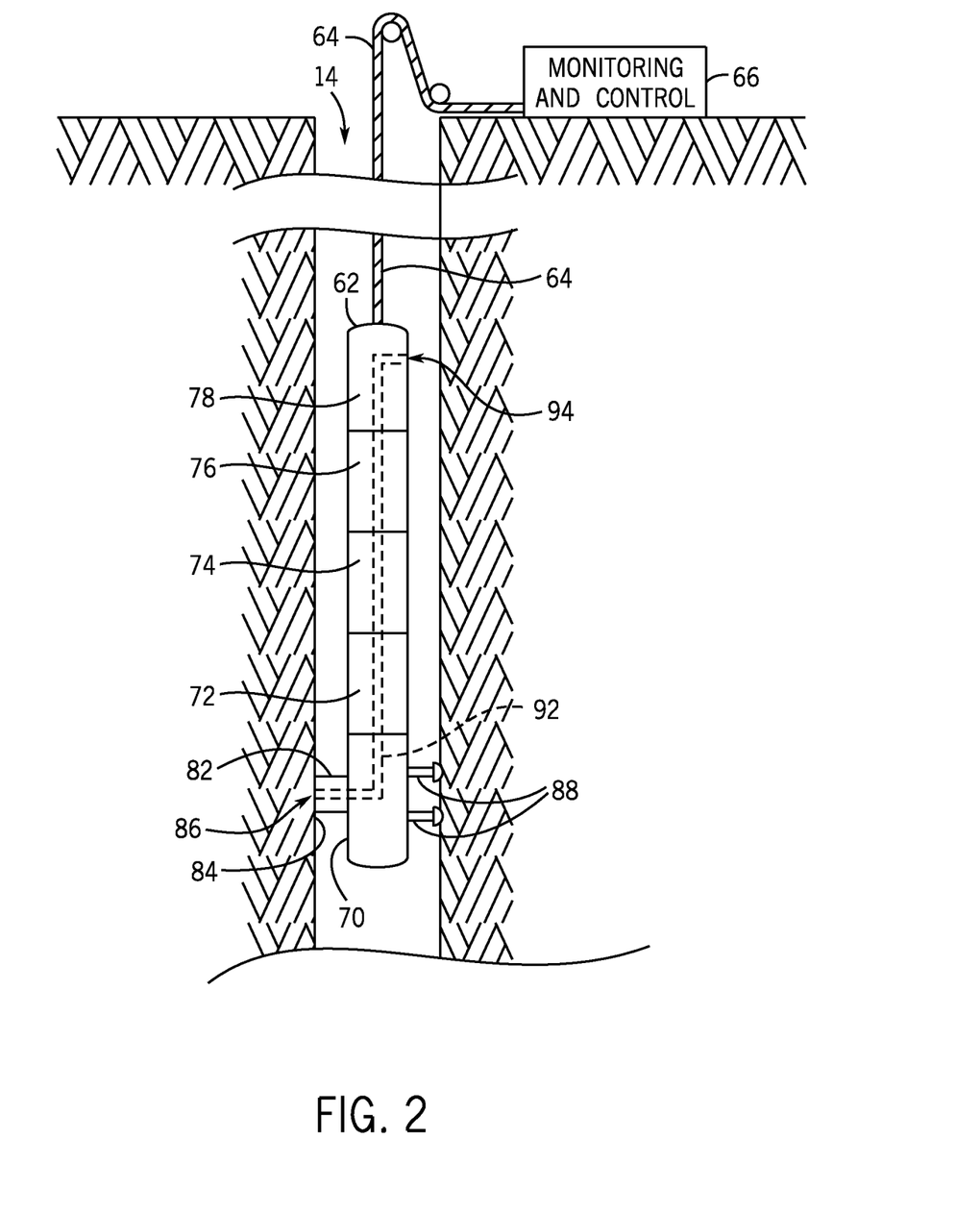
FIG. 2 generally depicts a fluid sampling tool deployed within a well on a wireline in accordance with one embodiment.

Another example of using a downhole tool for formation testing within the well 14 is depicted in FIG. 2. In this embodiment, a fluid sampling tool 62 is suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 controls movement of the fluid sampling tool 62 within the well 14 and receives data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) is incorporated into or as one or more modules of the bottomhole assembly 18, such as the LWD module 44 or the additional module 48.

The fluid sampling tool 62 can take various forms. While it is depicted in FIG. 2 as having a body including a probe module 70, a fluid analysis module 72, a pump module 74, a power module 76, and a fluid storage module 78, the fluid sampling tool 62 may include different modules in other embodiments. The probe module 70 includes a probe 82 that may be extended (e.g., hydraulically driven) and pressed into engagement against a wall 84 of the well 14 to draw fluid from a formation into the fluid sampling tool 62 through an intake 86. As depicted, the probe module 70 also includes one or more setting pistons 88 that may be extended outwardly to engage the wall 84 and push the end face of the probe 82 against another portion of the wall 84. In some embodiments, the probe 82 includes a sealing element or packer that isolates the intake 86 from the rest of the wellbore. In other embodiments the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 draws the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The fluid analysis module 72 includes one or more sensors for measuring properties of the sampled formation fluid, such as the optical density of the fluid, and the power module 76 provides power to electronic components of the fluid sampling tool 62.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Figure 3:
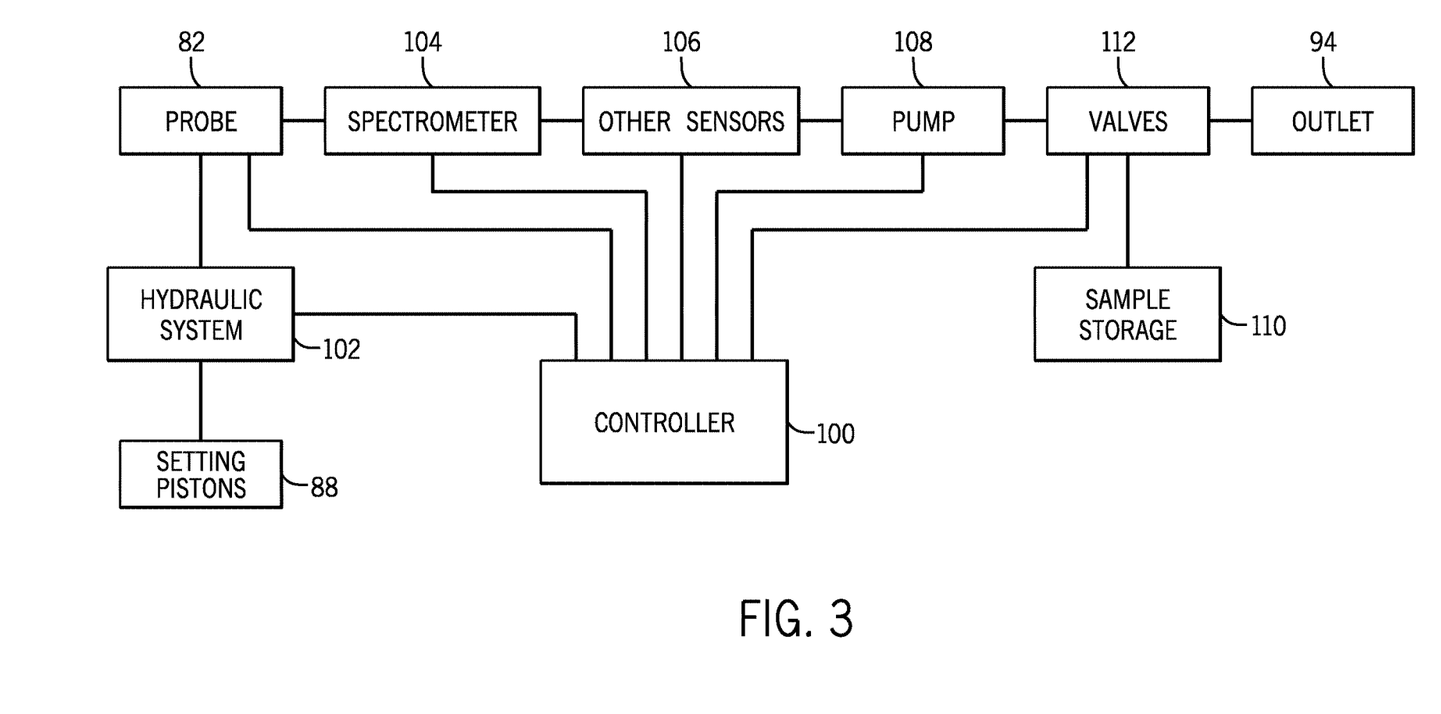
FIG. 3 is a block diagram of components of a fluid sampling tool operated by a controller in accordance with one embodiment.

Additional details as to the construction and operation of the fluid sampling tool 62 may be better understood through reference to FIG. 3. As shown in this figure, various components for carrying out functions of the fluid sampling tool 62 are connected to a controller 100. The various components include a hydraulic system 102 connected to the probe 82 and the setting pistons 88, a spectrometer 104 for measuring fluid optical properties, one or more other sensors 106, a pump 108, and valves 112 for diverting sampled fluid into storage devices 110 rather than venting it through the outlet 94.

In operation, the hydraulic system 102 extends the probe 82 and the setting pistons 88 to facilitate sampling of a formation fluid through the wall 84 of the well 14. It also retracts the probe 82 and the setting pistons 88 to facilitate subsequent movement of the fluid sampling tool 62 within the well. The spectrometer 104, which can be positioned within the fluid analysis module 72, collects data about optical properties of the sampled formation fluid. As discussed in greater detail below, such measured optical properties may include optical densities of the sampled formation fluid at one or more wavelengths of electromagnetic radiation. Other sensors 106 can be provided in the fluid sampling tool 62 (e.g., as part of the probe module 70 or the fluid analysis module 72) to take additional measurements related to the sampled fluid. In various embodiments, these additional measurements could include pressure and temperature, density, viscosity, electrical resistivity, saturation pressure, and fluorescence, to name several examples. Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 facilitates operation of the fluid sampling tool 62 by controlling various components. Specifically, the controller 100 directs operation (e.g., by sending command signals) of the hydraulic system 102 to extend and retract the probe 82 and the setting pistons 88 and of the pump 108 to draw formation fluid samples into and through the fluid sampling tool. The controller 100 also receives data from the spectrometer 104 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 also operates the valves 112 to divert sampled fluids from the flowline 92 into the storage devices 110.

Figure 4:
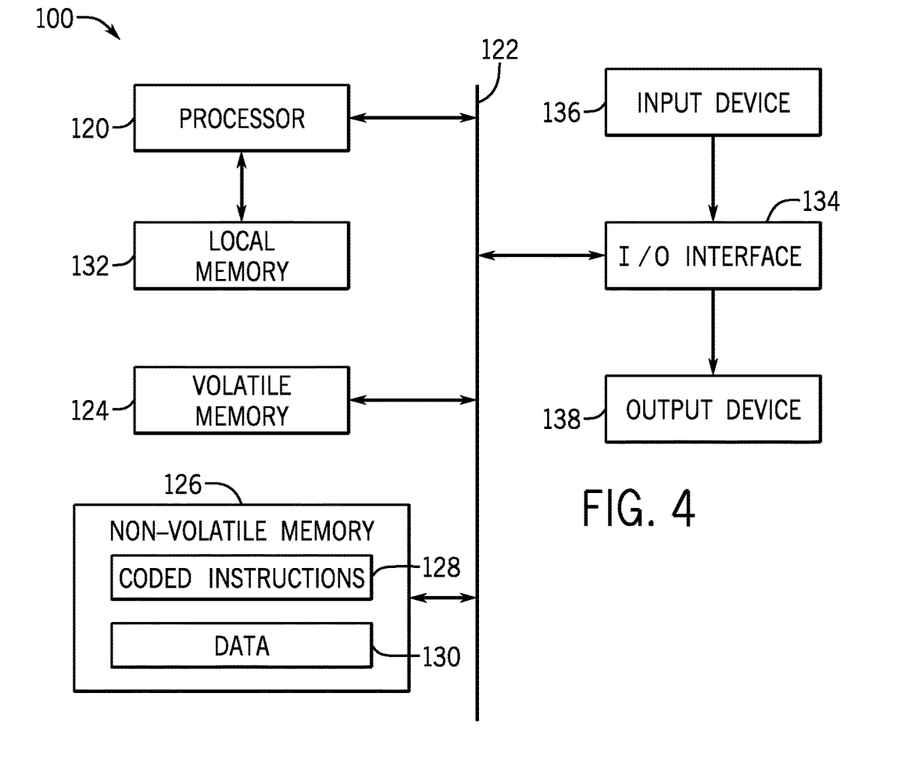
FIG. 4 is a block diagram of components in one example of the controller illustrated in FIG. 3.

The controller 100 in some embodiments is a processor-based system, an example of which is provided in FIG. 4. In this depicted embodiment, the controller 100 includes at least one processor 120 connected, by a bus 122, to volatile memory 124 (e.g., random-access memory) and non-volatile memory 126 (e.g., flash memory and a read-only memory (ROM)). Coded application instructions 128 (e.g., software that may be executed by the processor 120 to enable the control and analysis functionality described herein) and data 130 are stored in the non-volatile memory 126. For example, the application instructions 128 can be stored in a ROM and the data can be stored in a flash memory. The instructions 128 and the data 130 may be also be loaded into the volatile memory 124 (or in a local memory 132 of the processor) as desired, such as to reduce latency and increase operating efficiency of the controller 100.

An interface 134 of the controller 100 enables communication between the processor 120 and various input devices 136 and output devices 138. The interface 134 can include any suitable device that enables such communication, such as a modem or a serial port. In some embodiments, the input devices 136 include one or more sensing components of the fluid sampling tool 62 (e.g., the spectrometer 104) and the output devices 138 include displays, printers, and storage devices that allow output of data received or generated by the controller 100. Input devices 136 and output devices 138 may be provided as part of the controller 100, although in other embodiments such devices may be separately provided.

The controller 100 can be provided as part of the monitoring and control systems 56 or 66 outside of a well 14 to enable downhole fluid analysis of samples obtained by the fluid sampling tool 62. In such embodiments, data collected by the fluid sampling tool 62 can be transmitted from the well 14 to the surface for analysis by the controller 100. In some other embodiments, the controller 100 is instead provided within a downhole tool in the well 14, such as within the fluid sampling tool 62 or in another component of the bottomhole assembly 18, to enable downhole fluid analysis to be performed within the well 14. Further, the controller 100 may be a distributed system with some components located in a downhole tool and others provided elsewhere (e.g., at the surface of the wellsite).

Whether provided within or outside the well 14, the controller 100 can receive data collected by the sensors within the fluid sampling tool 62 and process this data to determine one or more characteristics of the sampled fluid. Examples of such characteristics include fluid type, gas-to-oil ratio, carbon dioxide content, water content, contamination, and, as discussed in greater detail below, asphaltene onset condition and yield.

Some of the data collected by the fluid sampling tool 62 relates to optical properties (e.g., optical densities) of a sampled fluid measured by the spectrometer 104. To facilitate measurements, in some embodiments the spectrometer 104 may be arranged about the flowline 92 of the fluid sampling tool 62 in the manner generally depicted in FIG. 5. In this example, the spectrometer 104 includes an emitter 142 of electromagnetic radiation, such as a light source, and a detector 144 disposed about the flowline 92 in the fluid sampling tool 62. A light source provided as the emitter 142 can be any suitable light-emitting device, such as one or more light-emitting diodes or incandescent lamps. As used herein, the term "visible light" is intended to mean electromagnetic radiation within the visible spectrum, and the shorter term "light" is intended to include not just electromagnetic radiation within the visible spectrum, but also infrared and ultraviolet radiation.

Figure 5:
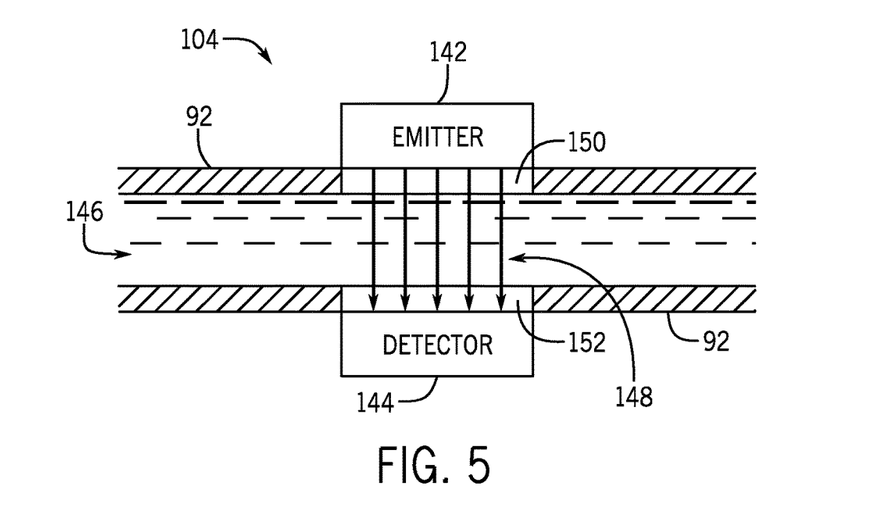
FIG. 5 generally depicts a spectrometer positioned about a flowline to enable measurement of an optical property of a fluid within the flowline in accordance with one embodiment.

In operation, a sampled formation fluid 146 within the flowline 92 is irradiated with electromagnetic radiation 148 (e.g., light) from the emitter 142. The electromagnetic radiation 148 includes radiation of any desired wavelengths within the electromagnetic spectrum. In some embodiments, the electromagnetic radiation 148 has a continuous spectrum within one or both of the visible range and the near-infrared range of the electromagnetic spectrum, and the detector 144 filters or diffracts the received electromagnetic radiation 148. The detector 144 may include a plurality of detectors each assigned to separately measure light of a different wavelength. As depicted in FIG. 5, the flowline 92 includes windows 150 and 152 that isolate the emitter 142 and the detector 144 from the sampled formation fluid 146 while still permitting the electromagnetic radiation 148 to be transmitted and measured. As will be appreciated, some portion of the electromagnetic radiation 148 is absorbed by the sampled fluid 146, and the extent of such absorption varies for different wavelengths and sampled fluids. The optical density of the fluid 146 at one or more wavelengths may be determined based on data from the spectrometer 104 by comparing the amount of radiation emitted by the emitter 142 and the amount of that radiation received at detector 144. It will be appreciated that the optical density (also referred to as the absorbance) of a fluid at a given wavelength is calculated as the base-ten logarithm of the ratio of electromagnetic radiation incident on the fluid to that transmitted through the fluid for the given wavelength.

The spectrometer 104 may include any suitable number of measurement channels for detecting different wavelengths, and may include a filter-array spectrometer or a grating spectrometer. For example, in some embodiments the spectrometer 104 is a filter-array absorption spectrometer having sixteen measurement channels. In other embodiments, the spectrometer 104 may have ten channels or twenty channels, and may be provided as a filter-array spectrometer or a grating spectrometer. Further, as noted above and described in greater detail below, the data obtained with the spectrometer 104 can be used to determine optical densities, asphaltene onset conditions, and asphaltene content of sampled fluids.

Figure 6:
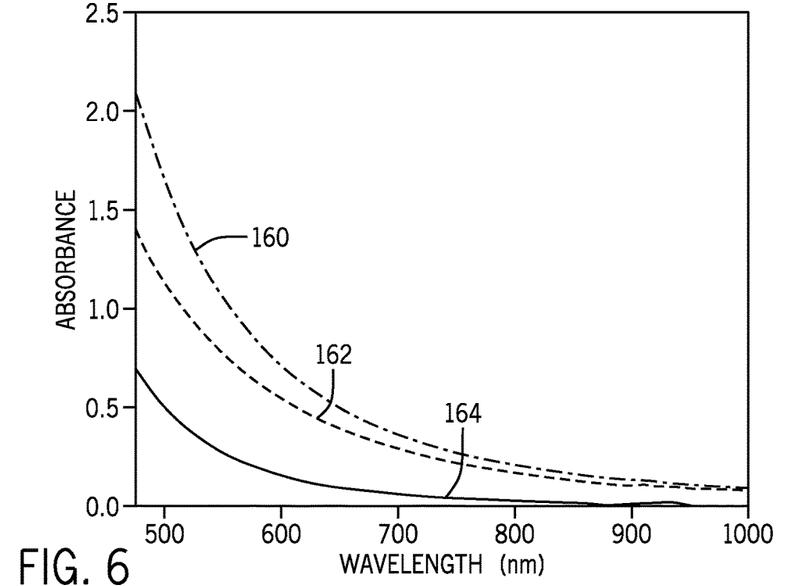
FIG. 6 is a graph representing optical spectra of a crude oil and its constituent maltenes and asphaltenes over visible and near-infrared wavelengths in accordance with one embodiment.

By way of example, FIG. 6 illustrates absorbance spectra for a crude oil and certain constituents of the crude oil. Particularly, this figure depicts an optical spectrum 160 for the crude oil, an optical spectrum 162 for the maltene portion of the crude oil, and an optical spectrum 164 for the asphaltene portion of the crude oil. It is noted that maltenes are the non-asphaltene portion of a crude oil and that these maltenes may include saturates, aromatics, and resins. The optical spectra of FIG. 6 are depicted as a function of wavelength of electromagnetic radiation, which ranges in the present figure from about 480 nm to 1000 nm (within the visible wavelength range and the near-infrared wavelength range).

It is possible to separate asphaltenes from a crude oil through various time-consuming, wet chemistry techniques. But one can also measure the optical spectrum of asphaltenes by subtracting the spectrum of maltenes from that of the crude oil. In certain conditions, asphaltenes in the crude oil aggregate (e.g., through flocculation) and can then be removed from the crude oil. This results in a difference in the optical spectra of the crude oil before and after removal of aggregated asphaltenes. In various embodiments, the absorbance of the crude oil before and after aggregated asphaltenes are removed is measured by optical spectroscopy. The crude oil is known to have higher absorbance than maltenes due to the presence of dissolved asphaltenes. The difference in optical absorbance in oil and maltenes can be used for detecting asphaltene onset condition and yield measurement in crude oils. As discussed in greater detail below, in at least some embodiments the asphaltene onset condition and yield measurement are determined as a function of pressure.

Figure 7:
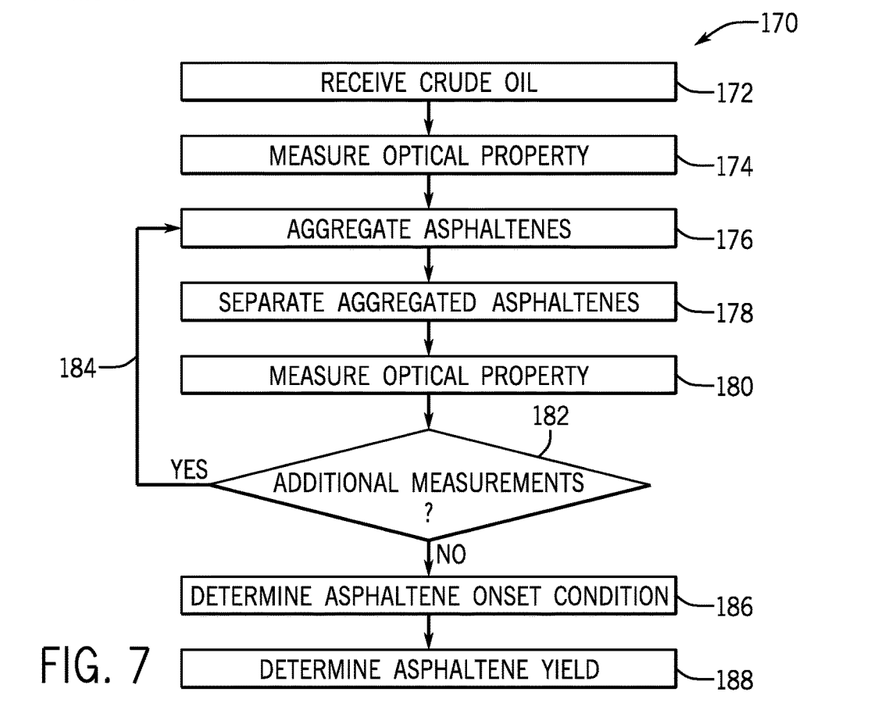
FIG. 7 is a flowchart for determining an asphaltene onset condition and asphaltene yield for a crude oil in accordance with one embodiment.

One example of a process for determining an asphaltene onset condition and yield of a crude oil is generally represented by flowchart 170 in FIG. 7. In this embodiment, a sample of a crude oil is received (block 172) in a measurement apparatus. For instance, a live crude oil may be sampled from a reservoir by a downhole tool (e.g., routed into the downhole fluid sampling tool 62) having the measurement apparatus. An optical property of the received crude oil is measured (block 174) within the measurement apparatus. In at least some embodiments, the measured optical property is an optical density of the crude oil, which can be measured by any of various suitable spectrometers, such as spectrometer 104 described above. Further, in at least some embodiments the optical density is measured using electromagnetic radiation within the visible or near-infrared wavelength ranges.

The method also includes aggregating asphaltenes (block 176) within the received crude oil, such as through flocculation or precipitation of the asphaltenes. In some embodiments, aggregation of asphaltenes is caused by lowering the pressure of the received crude oil within the measurement apparatus below its AOP. It will be appreciated that asphaltene aggregation could be caused in other ways, such as by lowering the temperature of the crude oil or adding another fluid to the crude oil. In at least some embodiments, however, depressurization of the crude oil is sufficient to cause asphaltene aggregation (without adding a different fluid or changing the temperature). After forming, aggregated asphaltenes are separated from the crude oil (block 178). In at least some instances, the crude oil containing aggregated asphaltenes is routed through a filter to separate the aggregated asphaltenes from the crude oil. Any suitable filter may be used, such as a high-pressure filter selected to retain aggregated asphaltene through steric rejection. The filtration can be performed in dead-end or cross-flow configuration or in combination to optimize system performance. To facilitate removal of aggregated asphaltenes from the crude oil, the mean pore size of the filter is 200 nm or less in at least some embodiments.

After separating the aggregated asphaltenes, an additional measurement of the optical property previously measured in block 174 is taken (block 180). For example, in an embodiment in which the crude oil is passed through a filter to remove aggregated asphaltenes, the optical density of the filtered crude oil can be measured with a spectrometer. If additional measurements are desired (decision block 182), the aggregation of asphaltenes, separation, and measurements of blocks 176, 178, and 180 can be repeated one or more times, as generally represented in FIG. 7 by iterative loop 184. As the optical spectrum of the removed asphaltenes is the difference between the optical spectra of the crude oil before and after removing the aggregated asphaltenes, the optical properties measured in blocks 174 and 180 can be compared to determine an asphaltene onset condition (e.g., AOP) of the crude oil received in the measurement apparatus (block 186). The measured optical properties can also be compared to determine asphaltene yield of the crude oil at one or more pressures (block 188). The determined asphaltene onset condition and yield could be communicated (e.g., to a user) or stored for later use.

The measurement processes described herein, such as the process generally represented by flowchart 170, can be carried out with any suitable measurement apparatus. For example, these processes can be carried out with a controller 100 in connection with a surface system or with a downhole tool (e.g., LWD module 44 or additional module 48 of FIG. 1, or fluid sampling tool 62 of FIG. 2) in a well. The measurement apparatus can use algorithms, executable code, lookup tables, and the like to carry out the functionality described above. Also, in some embodiments these processes may be performed in substantially real time without removing fluid samples from the well 14.

Figure 8:
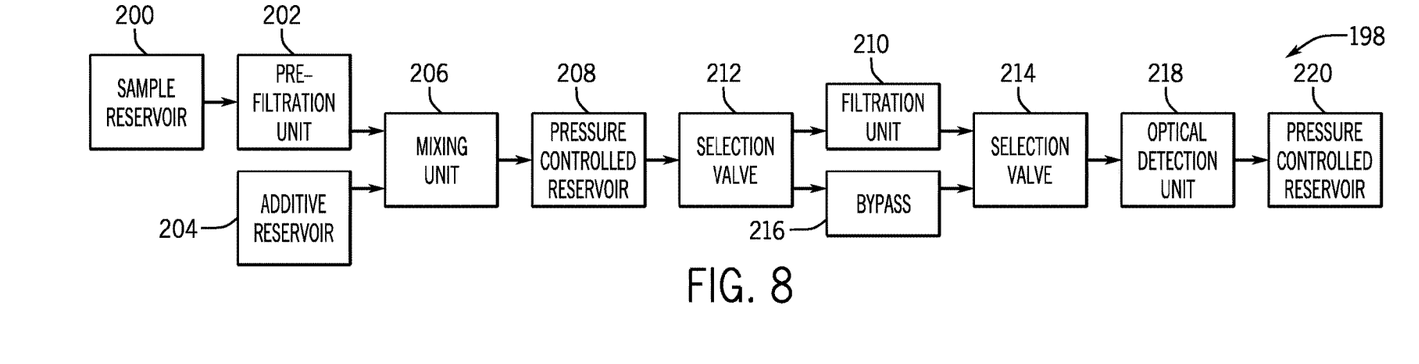
FIG. 8 is a block diagram of a measurement apparatus that can be used to analyze crude oils and determine asphaltene onset conditions and yields in accordance with one embodiment.
Figure 9:
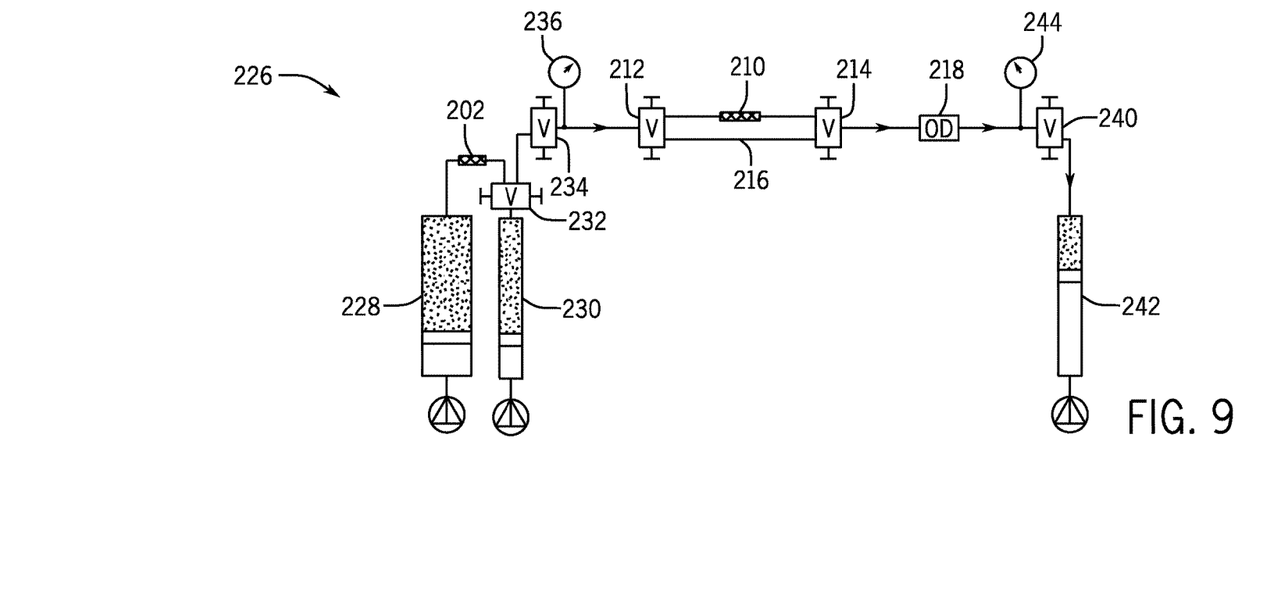
FIG. 9 generally depicts a measurement apparatus for determining asphaltene characteristics of a received crude oil in accordance with one embodiment.
Figure 10:
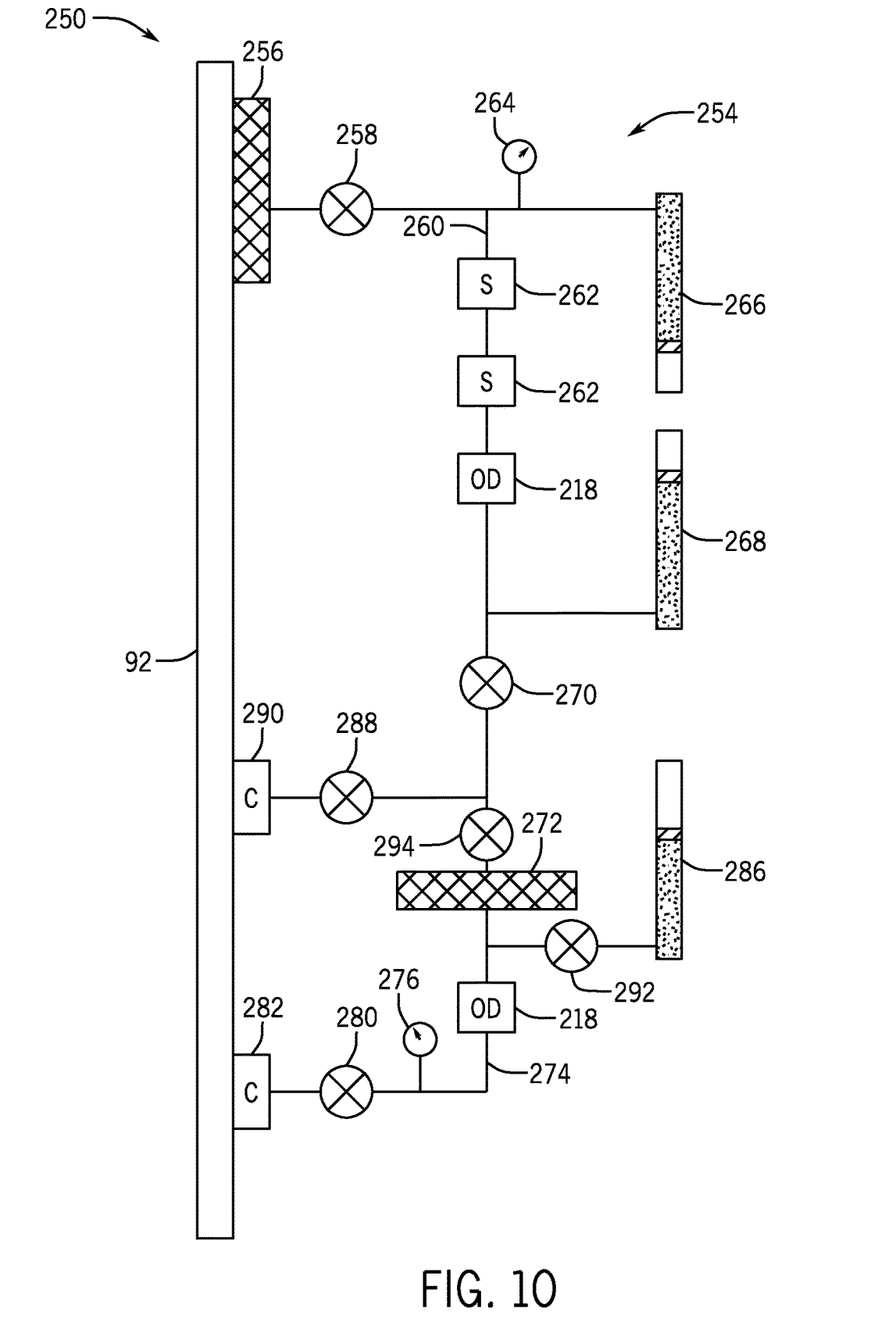
FIG. 10 generally depicts a measurement apparatus of a downhole tool for determining asphaltene characteristics of a crude oil received in the downhole tool in accordance with one embodiment.

Examples of such a measurement apparatus are generally depicted in FIGS. 8-10 in accordance with certain embodiments. It will be appreciated, however, that the measurement apparatus may take other forms, and may include other components in addition to or in place of those depicted in FIGS. 8-10. Although not separately depicted in FIGS. 8-10, the measurement apparatuses may include a controller 100 or another processor-based device that is used with the depicted components to determine asphaltene onset conditions and yields.

Referring first to FIG. 8, a measurement apparatus 198 is generally depicted as including a sample reservoir 200 (having a crude oil that is to be analyzed with the apparatus 198) and a pre-filtration unit 202. The sample reservoir 200 could be a fluid tank or bottle having the crude oil. In other instances, the sample reservoir 200 could be independent of the measurement apparatus 198. The reservoir 200 could be a subterranean hydrocarbon formation having the crude oil, for example. Crude oil from the reservoir 200 may be routed into a pressure-controlled reservoir 208 through the pre-filtration unit 202 (e.g., a filter) to remove particulates and emulsified water from the crude oil.

The apparatus 198 may also include an additive reservoir 204 and a mixing unit 206, as generally depicted in FIG. 8. In certain embodiments, some of which are described below, an additional fluid may be added to the crude oil from the additive reservoir 204 and then mixed into the crude oil via the mixing unit 206. In other embodiments, the measurement apparatus 198 does not include the additive reservoir 204 or the mixing unit 206.

The pressure ($P_{res}$) and temperature ($T_{res}$) of a live crude oil can be controlled in a measurement apparatus to facilitate determination of asphaltene precipitation. In at least some embodiments, a crude oil sample to be analyzed is maintained at a given temperature (e.g., the reservoir temperature in a downhole embodiment) and the pressure is changed in the pressure-controlled reservoir 208 to cause asphaltene aggregation, such as by moving a piston to increase the volume of the crude oil sample and reduce its pressure. The crude oil can be passed from the reservoir 208 to another pressure-controlled reservoir 220 through a filtration unit 210 to remove aggregated asphaltenes. The measurement apparatus 198 can include selection valves 212 and 214 that control flow of crude oil through the filtration unit 210 or a bypass line 216, which could be used to flow solvents through the apparatus if the filtration unit 210 becomes fouled and blocks flow. In other embodiments, however, the measurement apparatus 198 does not include the bypass line 216 or the selection valves 212 and 214. The apparatus 198 also includes an optical detection unit 218, such as a spectrometer 104 or other device suitable for measuring an optical property of the crude oil. The pressure of the crude oil (e.g., within reservoir 208) can be changed iteratively, and the AOP can be considered to be the highest pressure at which aggregated asphaltenes are detected (e.g., via differences in optical densities measured through optical spectroscopy).

The presently disclosed techniques for determining asphaltene onset conditions and yields may be implemented on a microfluidic platform or lab-on-a-chip system to reduce sample size and automate fluid handling and analysis. Processing time may be reduced by incorporating microfluidic components, such as microfluidic chaotic mixers and optical flow cells. In some embodiments, a microfluidic optical flow cell has a path length of less than three millimeters. A measurement apparatus may also include one or more microfluidic chips combined with conventional fluid handling or spectroscopy equipment in accordance with the present techniques.

In FIG. 9, a measurement apparatus 226 is shown as including sample fluid cylinders 228 and 230. These depicted cylinders include sealed pistons, and pressures in the cylinders are controlled by pumps. The measurement apparatus 226 also includes high-pressure stainless steel tubing (as flowlines) and various valves for controlling the flow of the sample fluid (e.g., crude oil) through the apparatus. The pre-filtration unit 202 between the fluid cylinders 228 and 230 can include a filter for removing debris or larger particulates from the sample. A valve 232 controls flow into and out of the cylinder 230. The depicted measurement apparatus 226 includes a filtration unit 210 (e.g., a 200 nm, inline filter), selection valves 212 and 214, a bypass line 216, and an optical detection unit 218. The filtration unit 210 can be used to remove aggregated asphaltenes from a crude oil sample and the optical detection unit 218 can be used to determine asphaltene onset conditions and yields, such as described above with respect to measurement apparatus 198. Additional valves 234 and 240 can be included to control flow of fluid between the cylinder 230 and an additional fluid cylinder 242. The apparatus 226 is also shown as having pressure sensors 236 and 244 for measuring fluid pressure upstream and downstream of the filtration unit 210. In at least some instances, temperature of the crude oil sample is generally maintained at a desired temperature, while the pressure is varied to cause asphaltene aggregation.

The flowline between the valve 232 and the cylinder 242 may initially be filled with a solvent (e.g., toluene) at reservoir pressure. A small pressure drop ($P_{step}$) can be created between cylinders 230 and 242 to flow the sample fluid to the cylinder 242 through the filtration unit 210 between valves 212 and 214 and displace the solvent. The inlet pressure ($P_1$, measured with pressure sensor 236), outlet pressure ($P_2$, measured with pressure sensor 244), and optical spectrum of the sample fluid (Optical Density versus wavelength, or OD) can be recorded at the average pressure $P_{average,1} = (P_1+P_2)/2$ and at $T_{res}$. The valve 212 can then be closed and the pressure in the cylinder 230 may be reduced, such as by a predefined value ($P_{step}$). As previously noted, the pressure may be reduced by increasing the volume of the sample fluid. The sample fluid can be agitated for a given period of time to ensure a well-mixed sample in the cylinder 230. Then, the pressure in cylinder 242 can be reduced (e.g., by $P_{step}$) and valve 212 can be opened to flow the depressurized sample through the filtration unit 210. The optical spectrum of fluid (OD) can be recorded at the average pressure $P_{average,2} = (P_1+P_2)/2$.

The pressure of the sample fluid can be lowered in stages, and after each depressurization the optical spectrum of the sample fluid can be compared to one or more of the previously obtained spectra. This procedure can be continued until a considerable drop in optical density (or some other optical property) is observed. A notable change in optical density would indicate a change in the color of the oil caused by asphaltene removal by the filtration unit 210. At this stage, the pressure is below onset asphaltene pressure (AOP). To accurately measure the AOP, the procedure may be repeated with refined pressure steps ($P_{step}$). Below AOP, the kinetics of the mixing process in cylinder 230 could be monitored by incorporating a second optical detection unit 218 before the filtration unit 210. Mixing elements can be added in cylinder 230 to enhance aggregate formation.

Following AOP measurement, pressure in cylinder 230 can be further decreased to cause more asphaltene aggregation, the aggregated asphaltenes could be filtered out of the sample fluid by filtration unit 210, and the optical density of the filtered sample (of the maltenes and any remaining, dissolved asphaltenes) can be measured. The difference in optical density between a crude oil sample above AOP and a filtered crude oil sample below AOP can be correlated with the weight concentration of asphaltene (yield measurement) at each pressure step. More specifically, after AOP is reached, successive decrements in pressure (below AOP) can be performed and the corresponding optical density can be measured. By subtracting the below-AOP optical density from the above-AOP optical density, the differential optical density can be determined. In this way, the amount of asphaltene flocculating or precipitating out of the solution (i.e., the asphaltene yield) at different pressures below the AOP can be acquired. The asphaltene yield as a function of pressure can then be extrapolated to zero to more precisely determine the AOP, if desired. Furthermore, the asphaltenes could be redissolved in the crude oil sample by successive pressure increments to study the reversibility of such asphaltene behavior.

At the end of the depressurization cycle, the flow path between valve 232 and valve 240 can be cleaned using solvents (e.g., toluene, xylene, 1-methylnaphthalene, or benzene) at $T_{res}$. In some embodiments the measurement apparatus 226 includes microfluidic components (such as tubing, optical cells, and other components) having small internal volumes, and precipitated asphaltene particles can be dissolved and removed by flowing a correspondingly small amount (e.g., several milliliters) of the solvent through the flowlines. Such microfluidic embodiments may facilitate downhole implementation of the present techniques, such as within a downhole formation testing tool. To ensure the same initial condition for each test, the optical density of the solvent can be measured prior to introducing a crude oil sample in optical detection unit 218 and can be used as a baseline during cleaning. The cleaning cycle can be continued until the optical density of the solvent stream reaches the baseline.

The measurement apparatus 226 can be modified to account for the kinetics of asphaltene flocculation or precipitation by having multiple optical detection units to interrogate the sample at different locations along the flow path (e.g., at different times) between the cylinders 230 and 242 or in these cylinders. The filtration unit 210 can be modified to facilitate multiple inline filters to increase filtration efficiency and reliability. Finally, different cylinder configurations can be implemented to facilitate sample injection or injection of other fluids.

In FIG. 10, a downhole tool system 250 is shown as having a measurement apparatus 254 for analyzing fluid drawn from a main flowline 92 of the tool. The system 250 can be provided as part of a downhole tool in a drill string, a downhole tool deployed by wireline, or some other downhole tool, such as those described above. The system 250 can be operated according to the techniques described above to determine asphaltene onset conditions and yields for formation fluids received in the tool (e.g., by systematically depressurizing crude oil drawn into the downhole tool, filtering aggregated asphaltenes, and comparing measured optical densities).

In the presently depicted embodiment, crude oil is drawn into the measurement apparatus 254 from the main flowline 92 through a membrane 256. The fluid in the flowline 92 may include water, and the membrane 256 of at least some embodiments is an oil-water separation membrane that inhibits flow of water to other components of the measurement apparatus 254. A valve 258 controls flow of crude oil into a measurement flowline 260. Various sensors 262, along with a pressure sensor 264, can be provided along the flowline 260 for measuring fluid characteristics. The measurement apparatus 254 also includes piston chambers 266 and 268, which can be used for mixing and depressurization of the crude oil within the flowline 260. Pressure of the crude oil within the flowline 260 can be changed by moving the piston of chambers 266 or 268 to change the volume of the crude oil. In some embodiments, the apparatus 254 is a microfluidic system, in which the sensors 262 are microfluidic sensors, the optical detection units 218 (e.g., spectrometers) are miniaturized units with optical path lengths of less than three millimeters (with at least one embodiment having an optical detection unit 218 with a path length of two millimeters), and the pistons of chambers 266 and 268 are micropistons.

A valve 270 can be opened to allow the crude oil to flow through an asphaltene filter 272 into a flowline 274 downstream of the filter 272. Like the filtration unit 210 above, the filter 272 collects aggregated asphaltenes in the crude oil, such as those formed from depressurization of the oil to a level below its AOP. Any suitable filter 272 could be used, and the filter 272 may be identical to the filter described above with respect to filtration unit 210. The pressure of the crude oil in the flowline 274 can be measured with a pressure sensor 276, and an optical property (e.g., optical density) of the crude oil in the flowline 274 can be determined with an optical detection unit 218 downstream from the filter 272. In at least one embodiment, such as that depicted in FIG. 10, an additional optical detection unit 218 is provided upstream of the filter 272 to allow measurement of optical density or another optical property of the crude oil before it is passed through the filter 272.

After analysis of the crude oil in the flowline 274, a valve 280 can be opened and the crude oil 274 may be discharged into the main flowline 92 through check valve 282. The measurement apparatus 254 also includes a piston chamber 286, which may be filled with a solvent for flushing asphaltenes collected by the filter 272 out of the downhole tool and into the well. For example, with the valves 270 and 280 closed and valve 288 open, solvent can be expelled from the piston chamber 286 (via its piston), through the filter 272, and out into the main flowline 92 through check valve 290 to be carried out of the downhole tool. In this manner, asphaltenes collected by the filter can be dissolved and discharged into the main flowline 92 with the solvent to flow out of the downhole tool. An isolation valve 292 can be used to isolate the solvent of piston chamber 286 from crude oil (or other fluids) in the flowline during various flow and measurement operations.

Further, the depicted measurement apparatus 254 also includes a valve 294, which can be closed during depressurization of the crude oil to isolate the filter 272 from the crude oil being depressurized in the flowline 260. The valve 294 can also be closed to allow discharge of the crude oil from the flowline 260 without passing through the filter 272 (e.g., when the crude oil in the flowline 260 does not possess an asphaltene signature). Additionally, the valve 294 can be closed during flushing of the filter 272 with solvent from piston chamber 286, which allows backflow of the solvent without passing through the flowline 260.

Figure 11:
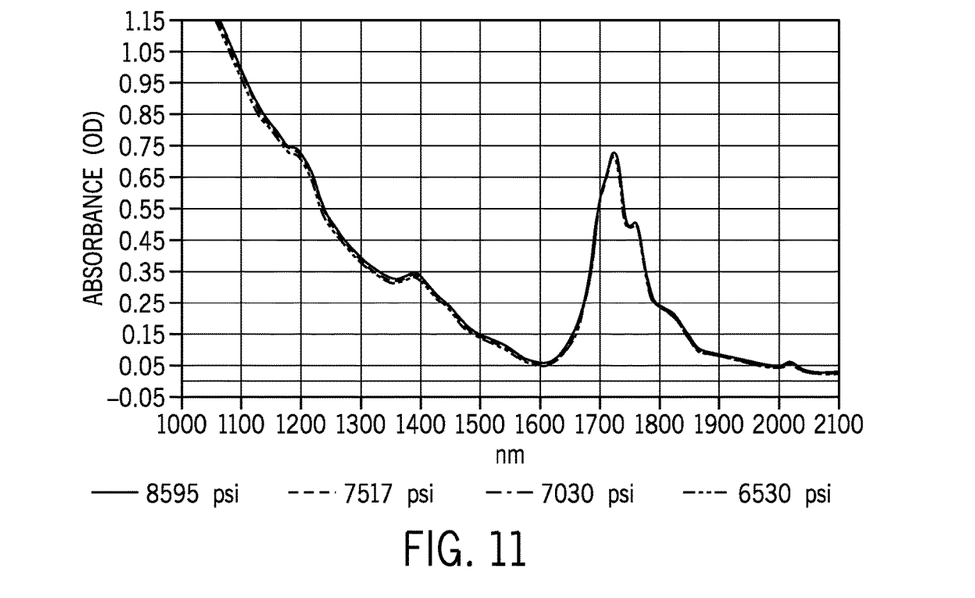
FIG. 11 graphically depicts optical spectra of a live crude oil at pressures above the asphaltene onset pressure of the crude oil in accordance with one embodiment.
Figure 12:
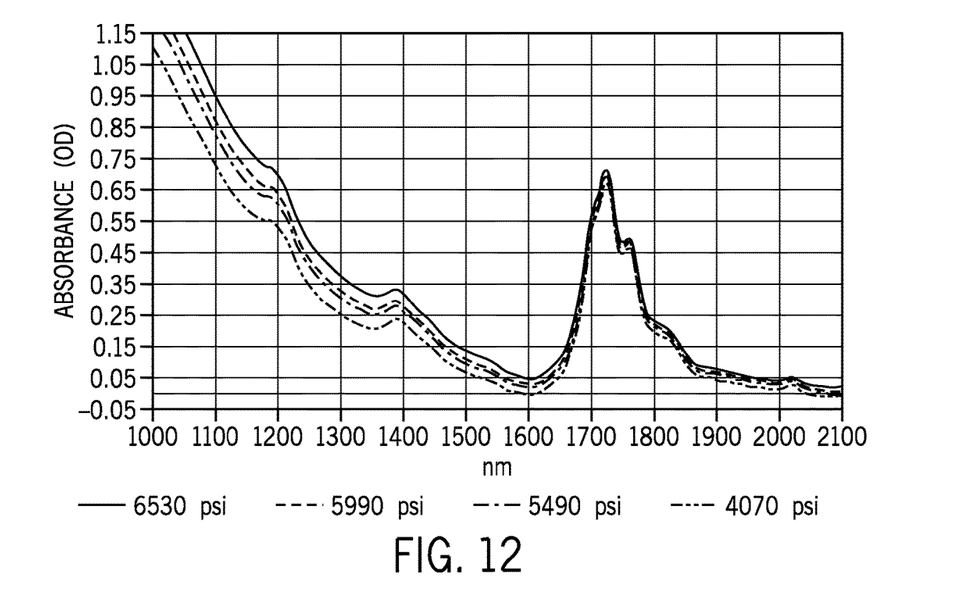
FIG. 12 graphically depicts additional optical spectra of the live crude oil of FIG. 11, but includes optical spectra at pressures below the asphaltene onset pressure of the crude oil, in accordance with one embodiment.

By way of further example, FIGS. 11 and 12 depict optical spectra of a live crude oil measured at various test pressures at a set reservoir temperature with a measurement apparatus in accordance with the present techniques. More specifically, the absorbance of the live crude oil at various pressures above its AOP is depicted in FIG. 11, while FIG. 12 depicts the absorbance of the live crude oil at one of the pressures depicted in FIG. 11 and at several other pressures below its AOP. The optical spectra depicted here for pressures below the AOP represent the absorbance of the live crude oil after removal of aggregated asphaltenes (e.g., as measured by pressure sensor 244 or 276). In this example, the AOP of the crude oil was independently measured to be 6,000 psi through a PVT lab technique. For pressures above AOP, the spectra are nearly identical, with just minor change in the spectra resulting from changes in mass density due to depressurization.

In contrast, the depicted spectra at pressures near and below AOP in FIG. 12 show notable changes in the absorbance of the filtered fluid as the tested pressures fall below AOP. Whereas the reduction of the test pressure from 8595 psi to 6530 psi had little effect on the spectra, the reduction of the test pressure from 6530 psi to 5990 psi was accompanied by a marked reduction in optical density of the filtered oil. This change may be attributed to asphaltene aggregation occurring in the crude oil once the test pressure was lowered below AOP. Further reductions in optical density can be observed for subsequent lowering of the test pressure.

Figure 13:
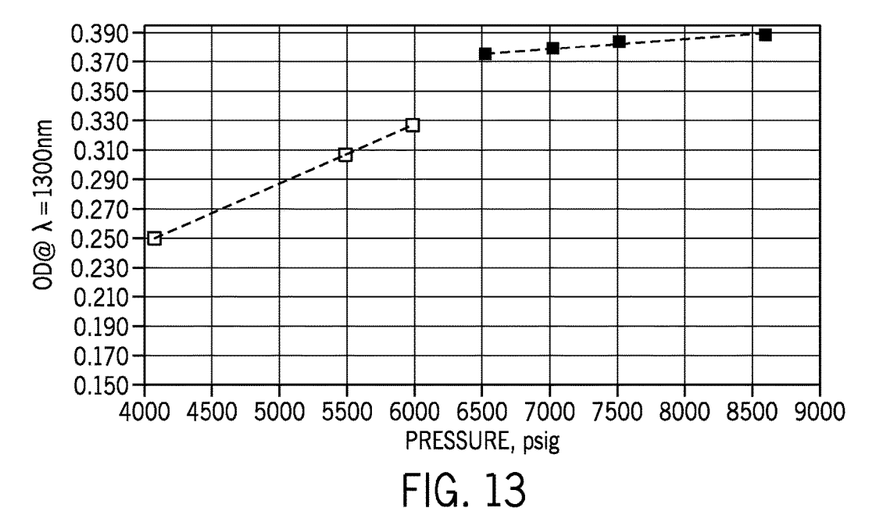
FIG. 13 is a graph plotting optical density of the crude oil at a wavelength against pressure, according to the optical spectra of FIGS. 11 and 12, in accordance with one embodiment.

For clarity, the absorbance at a single wavelength (1300 nm) is plotted as a function of pressure in FIG. 13. As generally noted above, the change in absorbance from 8595 psi to 6530 psi may be caused by the change in fluid mass density due to pressure change. The overall absorbance change in this pressure range is small compared to the absorbance change observed between 6530 psi and 5990 psi. Therefore, this data indicates that asphaltene aggregation begins to occur between 6530 psi and 5990 psi. At pressures below 5990 psi, the absorbance continues to drop which demonstrates further removal of additional aggregated asphaltenes formed in the oil below AOP. In this case, 5990 psi could be considered the AOP of the crude oil, or further measurements could be taken between 5990 psi and 6530 psi to more precisely identify the pressure range in which asphaltenes begin to aggregate and to more accurately determine the AOP.

The weight concentration of asphaltene (yield) aggregating as a function of pressure can be measured based on the present techniques. The reduced absorbance of maltenes plus dissolved asphaltenes (e.g., of a crude oil after separation of aggregated asphaltenes) at any pressure below AOP is an indication of how much asphaltene was removed from the oil at that pressure. Therefore, using differences between the absorbance of the maltenes (including any remaining dissolved asphaltenes) below AOP with the absorbance of oil at pressures above AOP, one can quantify the amount of aggregated asphaltene. Optical measurements performed under HPHT conditions can be translated to asphaltene yield weight percentages using correlations identified from prior testing. For instance, correlations between changes in optical density and asphaltene yield can be identified through testing of crude oil samples of varying content and from varying geographical regions. These correlations (or data derived from these correlations) may be stored in a lookup table for the controller 100 to access, allowing the controller 100 to determine asphaltene yield of a live crude oil based on the measured change in optical density as pressure is lowered below AOP.

Several other tests related to asphaltene study can be conducted using the presently disclosed techniques. Some of these tests use a second liquid or a gas added to the live crude oil in defined proportion to measure AOP and yield in the presence of the additive. To facilitate such tests, in one embodiment the cylinder 228 of measurement apparatus 226 (FIG. 9) holds the additive, which can be injected in a measured amount into the cylinder 230. The cylinder 230 can include an active mixer to prepare a homogenous mixture for analysis via the techniques described above. By way of example, these other tests can include: titration, in which a solvent (e.g., a light hydrocarbon) or gas (e.g., carbon dioxide, nitrogen, or a mixture of both) is injected into the sample at reservoir condition to measure AOP and yield; measuring total asphaltene content by forcing precipitation using normal alkanes at HPHT; an asphaltene inhibitor test, in which the performance of an asphaltene inhibitor can be evaluated at reservoir condition; and a fluid compatibility test, in which oils from different pay zones are mixed to cause asphaltene instability.

Although certain examples of using optical density measurements of crude oils to determine asphaltene onset conditions and yields are described above, other optical properties can also or instead be used to determine asphaltene onset conditions and yields. For example, refractive index measurements of a fluid sample in the systems described above (for both surface and downhole applications) can be used to detect the onset of asphaltene aggregation. In one embodiment, an additive (e.g., heptane) is added to a crude oil sample little by little. Above the onset condition (where the asphaltenes are stably dispersed in the mixture), the refractive index linearly decreases at a certain rate. At and below the onset condition, the asphaltenes start aggregating and are separated from the mixture, which results in the refractive index decreasing at a faster rate. The onset condition can be identified by detecting the change in the decreasing trend. In another embodiment, fluorescence measurements are used to detect the onset of asphaltene aggregation. The fluorescence intensity undergoes a step change when colloidally dispersed asphaltenes are precipitated, since the chance of the quenching (which is caused by electronic energy transfer from fluorescent molecules to colloidally dispersed asphaltenes and greatly reduces the fluorescence intensity) becomes less frequent. Consequently, measurement of the fluorescence allows identification of an asphaltene onset condition. In still other embodiments, light scattering (e.g., via side-angle and back-angle scattering techniques) could be used to identify an asphaltene onset condition.

The foregoing outlines features of several embodiments so that those skilled in the art may better understand aspects of the present disclosure. Those skilled in the art should appreciate that they may readily use the present disclosure as a basis for designing or modifying other processes and structures for carrying out the same purposes or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The invention claimed is:
1. A method comprising:
receiving a crude oil having an initial pressure and temperature within a downhole tool inside a well;
taking a first measurement of an optical density of the crude oil within the downhole tool;
causing aggregation of asphaltenes in the crude oil by lowering the pressure of the crude oil within the downhole tool after taking the first measurement of the optical property;
separating aggregated asphaltenes from the crude oil after lowering the pressure of the crude oil within the downhole tool, wherein separating aggregated asphaltenes from the crude oil includes routing the crude oil through a filter within the downhole tool to filter the aggregated asphaltenes from the crude oil;
taking a second measurement of the density of the crude oil within the downhole tool after separating aggregated asphaltenes from the crude oil;
determining an asphaltene onset condition of the crude oil through comparison of the first and second measurements of the optical property, wherein determining the asphaltene onset condition of the crude oil includes determining an asphaltene onset pressure of the crude oil;
determining asphaltene yield of the crude oil at the initial pressure through comparison of the optical density of the filtered crude oil at the initial pressure to the optical density of the crude oil in which asphaltenes have not been removed by the filter;

changing pressure of the received crude oil to a second pressure that causes aggregation of asphaltenes in the crude oil and is lower than the initial pressure of the crude oil received within the downhole tool;

passing the crude oil through a filter of the measurement apparatus, causing aggregated asphaltenes in the crude oil at the second pressure to be filtered from the crude oil; and determining asphaltene yield of the crude oil at the second pressure.

2. The method of claim 1, wherein the aggregation of asphaltenes in the crude oil is caused by lowering the pressure of the crude oil within the downhole tool after taking the first measurement of the optical property.

3. The method of claim 2, wherein lowering the pressure of the crude oil within the downhole tool includes moving a piston to increase a volume of the crude oil within the downhole tool.

4. The method of claim 1, comprising flushing the aggregated asphaltenes from the downhole tool using a solvent.

5. The method of claim 4, wherein flushing the aggregated asphaltenes from the downhole tool using the solvent is performed while the downhole tool is within the well.

6. A method comprising:

receiving crude oil within a measurement apparatus;

changing pressure of the received crude oil within the measurement apparatus to a first pressure that causes aggregation of asphaltenes in the crude oil;

passing the crude oil through a filter of the measurement apparatus, causing aggregated asphaltenes in the crude oil to be filtered from the crude oil;

tracking the optical density of the crude oil after the crude oil has passed through the filter over different pressures, and identifying an asphaltene onset pressure from the tracked optical density over the different pressures;

determining the asphaltene weight concentration within the crude oil at the first pressure through comparison of the optical density of the filtered crude oil at the first pressure to the optical density of the crude oil in which asphaltenes have not been removed by the filter;

changing pressure of the received crude oil to a second pressure that causes aggregation of asphaltenes in the crude oil;

passing the crude oil through a filter of the measurement apparatus, causing aggregated asphaltenes in the crude oil at the second pressure to be filtered from the crude oil; and determining the asphaltene weight concentration within the crude oil at the second pressure.

7. The method of claim 6, comprising measuring the optical density of the filtered crude oil at the first pressure and the optical density of the crude oil in which asphaltenes have not been removed by the filter with different spectrometers of the measurement apparatus that are on opposite sides of the filter.

8. The method of claim 6, wherein tracking the optical density of the crude oil includes measuring the optical density of the crude oil with a spectrometer of a downhole tool that includes the measurement apparatus.

9. An apparatus comprising:

a downhole sampling tool including an intake configured to receive a formation fluid within the downhole sampling tool and a downhole fluid analysis module having a spectrometer and configured to enable measurement of an optical property of the received formation fluid, wherein the downhole fluid analysis module includes a filter that is configured to remove aggregated asphaltenes within the downhole sampling tool from the formation fluid;

a controller operable to:

cause aggregation of asphaltenes in the received formation fluid within the downhole sampling tool by lowering a pressure of the received formation fluid to a first pressure;

pass the crude oil through a filter of the downhole fluid analysis module, causing aggregated asphaltenes in the crude oil to be filtered from the formation fluid;

measure the optical density of the formation fluid after the formation fluid has passed through the filter over different pressures;

identify an asphaltene onset pressure from the measured optical density over the different pressures;

determine asphaltene content of the received formation fluid at the first pressure through comparison of the optical density of the filtered received formation fluid at the first pressure to the optical density of the formation fluid in which asphaltenes have not been removed by the filter;

change pressure of the received formation fluid to a second pressure that causes aggregation of asphaltenes in the formation fluid;

pass the formation fluid through a filter of the measurement apparatus, causing aggregated asphaltenes in the crude oil at the second pressure to be filtered from the crude oil; and determine asphaltene content within the crude oil at the second pressure.

10. The apparatus of claim 9, wherein the controller is operable to lower the pressure of the received formation fluid by increasing the volume of a region holding the received formation fluid.

11. The apparatus of claim 9, wherein the controller is provided within the downhole sampling tool.

* * * * *